United States Patent [19]

Stein

[11] Patent Number: Plant 7,226

[45] Date of Patent: May 8, 1990

[54] EARLY EATING APPLE 'OR'

[75] Inventor: Abba Stein, Ein Shemer, Israel

[73] Assignee: Fruit Board, Tel Aviv, Israel

[21] Appl. No.: 219,059

[22] Filed: Jun. 29, 1988

[51] Int. Cl.[5] ..... A01H 5/00

[52] U.S. Cl. ..... Plt./34

[58] Field of Search ..... Plt. 34

*Primary Examiner*—James R. Feyrer

*Attorney, Agent, or Firm*—Browdy and Neimark

[57] ABSTRACT

An apple variety derived by hybridization from 27×Red Delicious×Anna $F_2$ is distinguished by the fact that it can be grown successfully without the necessity for an extreme degree of cold in the winter season, and that it may be harvested earlier than the nearest comparable variety.

3 Drawing Sheets

This invention relates to new and distinct variety of the apple *Malus sylvestrius L.*

The new apple was produced by hybridization 27×Red Delicious $F_2$. Propagation is by asexual reproduction (grafting of cuttings). The new variety has been examined over a period of three years at Ein Shemer and Moshav Maor, Israel. In Israel, the variety is grown in irrigated fields. The new variety has been tested for a period of two years by the Ministry of Agriculture, Plant Breeders' Rights Council, Bet Dagan, Israel. The fruit of the new variety is red in color, and oblong conical in shape; the size is generally 6.5–7.5 cm., but can be up to 8–9 cm., in diameter. In Israel, the new variety flowers in March, and the apples are harvested in the first half of August. In appearance, the fruit of the new variety resembles the "Orleans" apple, but ripens some 2–3 weeks earlier. The apple of the invention is suitable for eating in the fresh state.

DESCRIPTION OF THE TREE, SHOOTS AND FLOWERS

Figure 1:
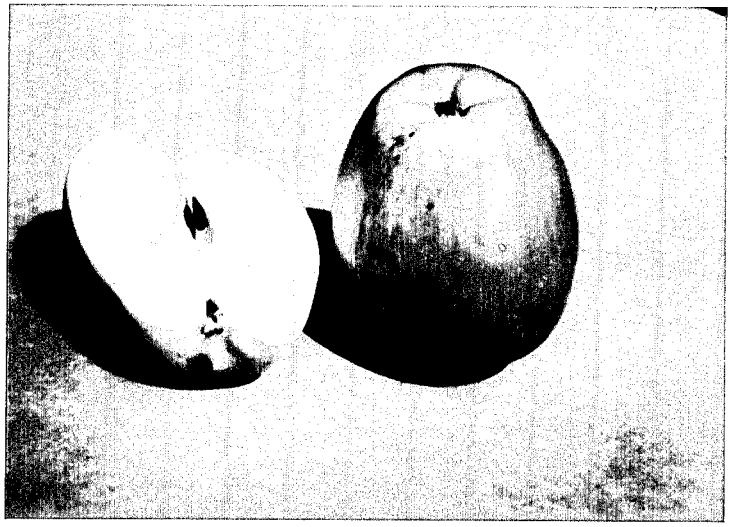
FIG. 1 is a photograph of respective whole and cut samples of ripe apples of the variety described, in which the cut sample clearly shows the elongated shape of the locules and seeds.
Figure 2:
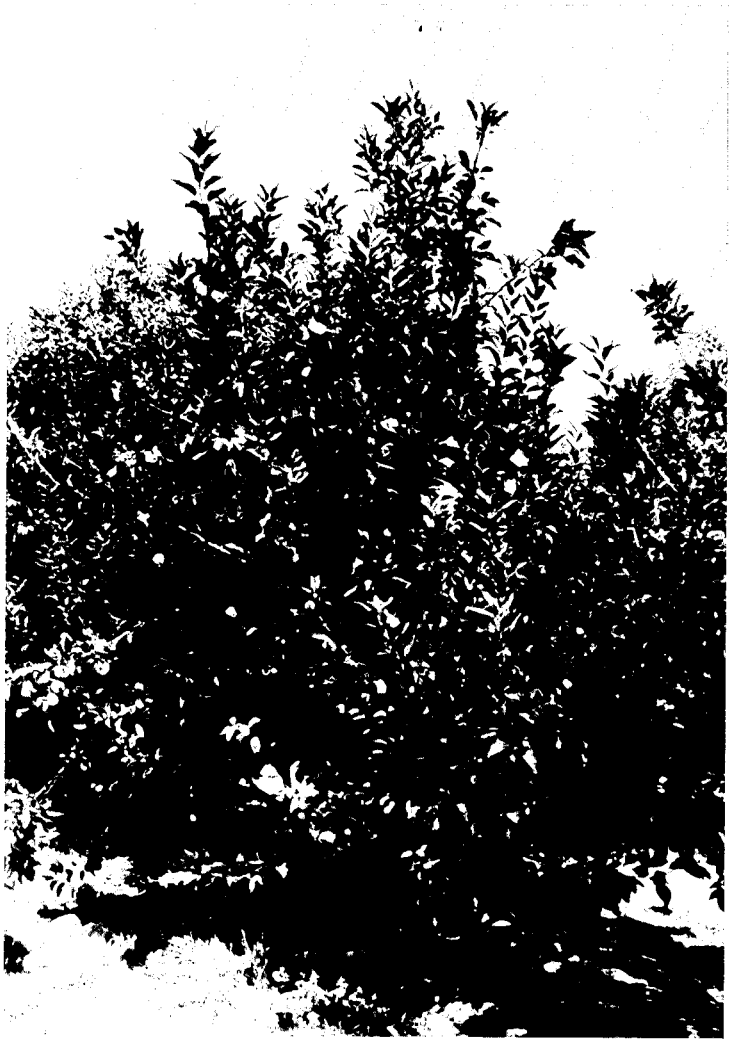
FIG. 2 is a photograph of a fruit-laden tree of the variety described.
Figure 3:
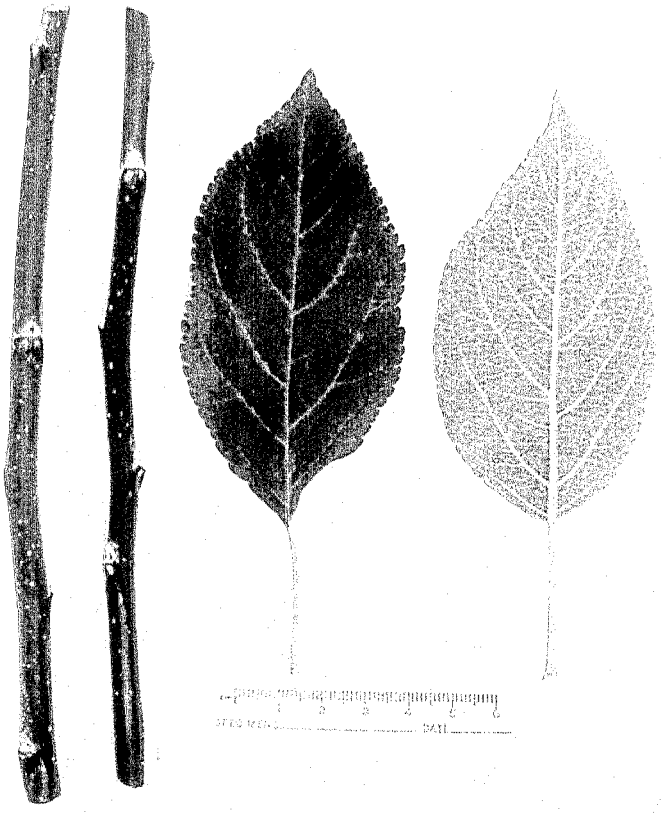
FIG. 3 is a photograph of twigs and leaves of the subject variety. The one year old shoots shown have a zigzag tendency with large buds and medium sized lenticels. The lower side of the leaf (on the right side of the photograph) has very weak anthocyanin coloration of the veins. The upper side of the leaf (in the middle of the photograph) is a dark green color.

The tree is of natural upright habit. On MALUS communis rootstock ultimate size is 6 m high and 5 m wide. The density of branches is sparse. The yearly growth is very vigorous and the growth of the shoots is zig-zag and fruit is borne predominantly on spurs. The characteristics of a one year old shoot are as follows: strong pubescence on upper half, strong shine on the bark, thickness (diameter at center) about 9 mm., medium flexibility, 9 nodes per 20 cm., medium number of small size lenticels, predominant color on the sunny side—brown (RHS-200C), large bud with pointed tip, position of bud relative to axis—adpressed, large bud support and weak crimping thereof. The flower bud is light pink just before the flower opens, the pedicel is green. The large single flower has broad elliptic petals, the petal margins are free, the color of the petal upper side is 55D (RHS Color Chart) and white when faded. Productivity is good and pollination is required with varieties flowering at the same time. Fruits are set in clusters and appropriate thinning is required.

DESCRIPTION OF THE LEAF

The leaf is of medium size, concave in cross-section, shape of the apex mucronate. The leaf blade, which is colored green (RHS-135C) when expanding, shows crenate indentation of margin, weak glossiness of the upper side, strong pubescence on the lower side and very weak anthocyanin coloration of the veins. The upper side, from which anthocyanin coloration is absent, is dark green (RHS-135A).

FRUIT CHARACTERISTICS

The fruit size is classified as large to very large, being generally at least 6.5–7.5 cm., or even up to 8–9 cm., in diameter. The shape is oblong conical, and asymmetric in side view. Ribbing is absent or very weak. There is a medium degree of crowning at the distal end. The eye is open and is of large size; there is a deep basin at the eye end of the fruit, the basin width being medium. Persistence of the calyx is present. The spacing of long sepals is free at the base. The fruit stalk is of medium thickness; the stalk cavity is deep, but is narrow. The fruit has a smooth surface, skin bloom is present; greasiness, translucency and cracking tendency of the skin are all absent. The skin is of medium thickness, its ground color is yellow (RHS-11A), the amount of the purple (RHS-46A) over color of the skin is very high, the over color being partly solid flush, partly streaked. The amount of russet, which is found around the stalk cavity, is very low. The lenticels are of medium size. The flesh is firm, juicy, greenish in color (RHS-149C-D) and has a fine texture; grittiness is absent. Any browning of the flesh one hour after being cut with a stainless steel knife is either absent or very weak. The fruit in cross section shows medium distinctiveness of the core and open aperture of locules. The number of locules is 5, the number of seeds varies between 5 and 10, the locules and seeds being elongated in shape. Both the time of picking for commercial harvest and the time of fruit ripening for eating are (in Israel) mid-August. Response to drought: full irrigation is required. No special sensitivity or resistance to insects or to diseases has been noticed. Salt tolerance medium and variations depend on the rootstocks used.

The keeping quality of the fruit is good and the fruit can be kept on the tree until fully ripe.

We have designated the new variety "Or". This new variety possesses the advantage (as mentioned previously) that it can be harvested earlier than the nearest comparable varieties, and moreover that it can be grown successfully without the necessity of the extreme degree of cold in the winter season, as has usually been necessary hitherto. This means of course that the apple has the potential for being grown in climates with winters which are relatively milder than climates in which apples are usually grown.

I claim:

1. The new and distinct variety of eating apple substantially as described and illustrated herein, being derived by hybridization from 27 × Red Delicious $F_2$ and distinguished by the fact that it can be grown successfully without the necessity for an extreme degree of cold in the winter season, and that it may be harvested earlier than the nearest comparable variety.

* * * * *